US007202225B1

(12) United States Patent
Emanuele et al.

(10) Patent No.: US 7,202,225 B1
(45) Date of Patent: *Apr. 10, 2007

(54) THERAPEUTIC DELIVERY COMPOSITIONS AND METHODS OF USE THEREOF

(76) Inventors: R. Martin Emanuele, 5320 N. Hillbrook Trace, Alpharetta, GA (US) 30202; Konstantin G. Kousoulas, 10543 N. Myrtle Lake Ave., Baton Rouge, LA (US) 70810; Hameedsulthan S. Allaudeen, 5211 Oakbrook Dr., Durham, NC (US) 27713

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/457,771

(22) Filed: Dec. 9, 1999

Related U.S. Application Data

(63) Continuation of application No. 09/104,088, filed on Jun. 24, 1998, now abandoned, which is a continuation-in-part of application No. 08/926,297, filed on Sep. 5, 1997, now abandoned, which is a continuation of application No. 08/725,842, filed on Sep. 30, 1996, now abandoned, which is a continuation of application No. 08/138,271, filed on Oct. 15, 1993, now abandoned.

(51) Int. Cl.
*A61K 31/715* (2006.01)
*A61K 31/08* (2006.01)
*A61K 47/32* (2006.01)
*C07C 43/00* (2006.01)

(52) U.S. Cl. ............... 514/44; 536/24.5; 514/723; 514/772.3; 568/624

(58) Field of Classification Search ............. 514/2, 514/8, 21, 152, 772, 311, 672, 723, 44; 424/78.38, 424/65, 280.1; 435/7.32, 320.1; 568/264, 568/624; 536/24.5, 23.1
See application file for complete search history.

(56) References Cited

U.S. PATENT DOCUMENTS

| 2,674,619 A | 4/1954 | Lundsted ............... 560/198 |
| 2,854,378 A | 9/1958 | Buckwalter ............ 514/152 |
| 2,979,528 A | 4/1961 | Lundsted ............... 564/505 |
| 3,022,335 A | 2/1962 | Lundsted ............... 536/120 |
| 3,036,118 A | 5/1962 | Jackson et al. ........ 560/182 |
| 3,089,818 A | 5/1963 | Stone ................... 525/54.1 |
| 3,140,232 A | 7/1964 | Noseworthy ............ 514/2 |
| 3,228,834 A | 1/1966 | Gans et al. ............ 514/21 |
| 3,450,502 A | 6/1969 | Hymes ................. 422/45 |
| 3,577,522 A | 5/1971 | Hymes ................ 424/78.38 |
| 3,590,125 A | 6/1971 | Hymes ................ 424/78.38 |
| 3,641,240 A | 2/1972 | Hymes et al. ......... 424/78.38 |
| 3,740,421 A | 6/1973 | Schmolka ............. 424/65 |
| 3,867,521 A | 2/1975 | Miskel et al. |
| 3,867,533 A | 2/1975 | Schmolka ............ 514/311 |
| 3,956,259 A | 5/1976 | Garcia et al. ......... 530/380 |
| 4,073,886 A | 2/1978 | Kehm ................ 530/383 |
| 4,100,271 A | 7/1978 | Krezanoski .......... 514/11 |
| RE29,909 E | 2/1979 | Kurtz ............... 514/772 |
| 4,323,560 A | 4/1982 | Baschang et al. ...... 514/8 |
| 4,395,393 A | 7/1983 | Schmolka ............ 514/672 |
| 4,407,790 A | 10/1983 | Oakes et al. ......... 514/723 |
| 4,409,209 A | 10/1983 | Baschang et al. ...... 514/8 |
| 4,410,660 A | 10/1983 | Straus ................ 525/54.1 |
| 4,423,038 A | 12/1983 | Baschang et al. ...... 514/8 |
| 4,489,158 A | 12/1984 | Straus ............... 435/7.32 |
| 4,575,484 A | 3/1986 | Straus ............... 435/7.32 |
| 4,606,918 A | 8/1986 | Allison et al. ........ 424/279.1 |
| 4,609,546 A | 9/1986 | Hiratani ............. 424/78.3 |
| 4,772,466 A * | 9/1988 | Allison et al. ........ 424/209.1 |
| 4,801,452 A | 1/1989 | Hunter et al. ........ 424/94.63 |
| 4,837,014 A | 6/1989 | Hunter et al. ........ 424/94.63 |
| 4,869,900 A | 9/1989 | Pozzi et al. .......... 424/94.1 |
| 4,873,083 A | 10/1989 | Hunter et al. ........ 424/1.49 |
| 4,879,109 A | 11/1989 | Hunter ............... 514/723 |
| 4,897,263 A | 1/1990 | Hunter ............... 514/723 |

(Continued)

FOREIGN PATENT DOCUMENTS

| DE | 27 08 152 | 9/1977 |
| EP | 0 000 704 | 2/1979 |
| EP | 0003999 | 2/1979 |
| EP | 0 003 999 | 9/1979 |
| EP | 0 011 237 | 5/1980 |

(Continued)

OTHER PUBLICATIONS

Verma et al. Nature 389: 239-242, especially p. 239, Sep. 1997.*
Anderson et al. Nature 392: 25-30, especially pp. 25 and 30, Apr. 1998.*

(Continued)

*Primary Examiner*—Richard Schnizer
(74) *Attorney, Agent, or Firm*—Townsend and Townsend and Crew LLP

(57) ABSTRACT

The present invention relates to compositions and methods for delivery of antisense oligonucleotides or other nucleic acid sequences. The present invention comprises a delivery composition comprising an administerable admixture of an effective amount of a nucleic acid sequence and an effective amount of a surface active nonionic block copolymer having the following general formula:

$$HO(C_2H_4O)_b(C_3H_6O)_a(C_2H_4O)_bH$$

wherein a is an integer such that the hydrophobe represented by $(C_3H_6O)$ has a molecular weight between approximately 750 and approximately 15,000, preferably between approximately 2250 and approximately 15,000, more preferably between approximately 3250 and approximately 15,000, and b is an integer such that the hydrophile portion represented by $(C2H4O)$ constitutes approximately 1% to approximately 50% by weight of the compound, preferably approximately 5% to approximately 25%.

5 Claims, 5 Drawing Sheets

U.S. PATENT DOCUMENTS

| | | | | |
|---|---|---|---|---|
| 4,937,070 | A | 6/1990 | Hunter | 424/78.38 |
| 4,997,644 | A | 3/1991 | Hunter | 424/78.35 |
| 5,017,370 | A | 5/1991 | Hunter et al. | 424/78.38 |
| 5,028,599 | A | 7/1991 | Hunter | 514/83 |
| 5,030,448 | A | 7/1991 | Hunter | 424/78.38 |
| 5,032,394 | A | 7/1991 | Hunter | 424/78.38 |
| 5,037,644 | A | 8/1991 | Shaked et al. | 424/85.2 |
| 5,039,520 | A | 8/1991 | Hunter | 424/78.38 |
| 5,041,288 | A | 8/1991 | Hunter | 424/78.38 |
| 5,047,236 | A | 9/1991 | Hunter et al. | 424/78.38 |
| 5,064,643 | A | 11/1991 | Hunter et al. | 424/78.38 |
| 5,071,649 | A | 12/1991 | Hunter | 424/78.38 |
| 5,078,995 | A | 1/1992 | Hunter et al. | 424/78.38 |
| 5,080,894 | A | 1/1992 | Hunter et al. | 424/78.38 |
| 5,089,260 | A | 2/1992 | Hunter et al. | 424/78.38 |
| 5,221,495 | A | 6/1993 | Cao | 435/188 |
| 5,262,170 | A | 11/1993 | Anderson et al. | |
| 5,372,928 | A * | 12/1994 | Miyamura | 435/5 |
| 5,376,369 | A * | 12/1994 | Allison et al. | 424/278.1 |
| 5,459,127 | A * | 10/1995 | Felgner et al. | 514/7 |
| 5,470,568 | A * | 11/1995 | Lee | 424/78.02 |
| 5,567,859 | A * | 10/1996 | Emanuele | 568/624 |
| 5,583,032 | A * | 12/1996 | Torrence | 435/91.1 |
| 5,656,275 | A * | 8/1997 | Wasmoen et al. | 424/199.1 |
| 5,674,911 | A * | 10/1997 | Emanuele et al. | 514/723 |
| 5,811,088 | A * | 9/1998 | Hunter et al. | 424/78.08 |

FOREIGN PATENT DOCUMENTS

| | | |
|---|---|---|
| EP | 0 049 422 | 9/1981 |
| EP | 0 103 290 | 9/1983 |
| EP | 0 121 752 | 10/1984 |
| EP | 0135376 | 7/1990 |
| FR | 2 081 436 | 1/1971 |
| JP | 60-105630 | 6/1985 |
| WO | PCT/US86/01747 | 8/1986 |
| WO | PCT/US87/01067 | 5/1987 |
| WO | WO 87/06836 | 11/1987 |
| WO | WO91/19794 | 12/1991 |
| WO | WO 92/16484 | 10/1992 |
| WO | WO 93/08845 | 5/1993 |
| WO | WO 99/39733 * | 8/1999 |

OTHER PUBLICATIONS

Orkin (Report and Recommendations of the Panel to Assess the NIH Investment in Research on Gene Therapy, see p. 1, item 3, and p. 9, Dec. 1995.*
Simons et al (Sep. 1992) Nature 359:67-70.*
Robinson-Benion et al (Antisense Research and Development, 1(1): 21-33, Feb. 1991.*
Branch. Trends in Biochemical Sciences 23: 45-50, especially p. 45, col. 3. first para., p. 48, last para. through p. 49, Feb. 1998.*
Crook In Basic Principles of Antisense Therapeutics, Springer-Verlag, Eds, New York, pp. 1 and 4. Jul. 1998Branch. Trends in Biochemical Sciences 23: 45-50, especially p. 45, col. 3. first para., p. 48, last para. through p. 49. Feb. 1998.Crook In Bas.*
Donelly et al (J Immunol. Meth. 176:145-152, See p. 150, col. 1, first full paragraph, and col. 2, first full paragraph, Dec. 1994.*
McCluskie et al (Molecular Medicine 5(5): 287-300, 1999.*
Bioccha et al (Cytotechnology 5 S49-50, 1991).*
Conforth, et al., "Antituberculous Effect of Certain Surface-Active Ethylene Ethers in Mice," Chemical Abstracts, vol. 46, No. 2696 (1952).
Schmolka, "A Review of Block Polymer Surfactants," Journal of the American Oil Chemists Society, vol. 54, No. 3, pp. 110-116 (1977).
Block and Graft Copolymerization, vol. 2, ed. by R.J. Ceresa, John Wiley & Sons (1976).

Matsukara, et al. "Phosphorothioate Analogs of Oligodeoxynucleotides: Inhibitors of Replication and Cytopathic Effects of Human Immunodeficiency Virus," Proc. Natl. Acad. Sci. USA, vol. 84, pp. 7706 (1987).
Moore, et al., "Reduction of Splenic Vascular Resistance During Profusion by Pluronic® F-68," Journal Surgical Research, vol. 8, pp. 563-566 (1968).
Snippe, et al., "Adjuvant Effect of Nonionic Block Polymer Surfactants in Humoral and Cellular Immuniology", Int. Archs Allergy Appl. Immun. vol. 65, pp. 390-398 (1981).
Byars, et al., "Adjuvant formulation for us in Vaccines to Elicit Both Cell-mediated and Humoral Immunology", Vaccine, vol. 5, pp. 223-228 (1987).
Paton, et al., "The Use of a Nonionic Detergent Added to Organ Perfusates," Organ Perfusion and Preserv., ed. by Norman, J.C. Appleton-Century-Crofts, pp. 105-120 (1968).
Technical Bulletin entitled "Pluronic® Block Copolymer Surfactants".
Hunter, et al. "Nonionic Block Copolymers Surfactants as Immunological Adjuvants: Mechanisms of Action and Novel Formulations," Immunological Adjuvants and Vaccines, ed. by Gregoriadis, G. et al., Plenun Publishing Corp., pp. 133-144 (1989).
Hunter, et al. "The Adjuvant Activity of Nonionic Block Polymer Surfactants. I. The Role of Hydrophile-Lipophile Balance," J. Immun., vol. 127, No. 3 (1981).
William, et al., "Modulation of Rat Granulocyte Traffic by a Surface Active Agent in Vitro and Bleomycin Injury," Proceedings of the Society for Experimental Biology and Medicine, vol. 188, pp. 461-470 (1988).
Block, et al. "Acutely Traumatized Canine Ureter. Effects of Low Molecular Weight Dextran and Surfactant Pluronic® F-68," Urology, vol. 3, No. 2, pp. 190-194 (1974).
Knize, et al. "Use of Antisludging Agents in Experimental Cold Injuries," Surgery, Gynecology & Obstetric, vol. 129, pp. 1019-1026 (1969).
Gaehtgens, et al., "Disaggregation of Human Red Blood Cells by Various Surface-Active Agents as Related to Changes of Cell Shape and Hemolysis," Act Heamat. vol. 53, pp. 82-89 (1975).
Lane, et al., "Reduction in the Toxicity of a Component of an Artificial Blood Substitute by Supercritical Fluid Fractionation," Transfusion, vol. 28, pp. 375-378 (1987).
Atkinson, et al., "Ion Transport Mediated by Copolymers Composed of Polyoxyethylene and Polyoxypropylene," pp. C20-C26 (1988).
Ketchum, L.D., "Pharmacoloigcal Alterations in the Clotting Mechanism: Use in Microvascular Surgery," Journal of Hand Surgery, vol. 3, pp. 407-415 (1978).
Benner, et al. "Uber die Wirkung von Pluronic® F-68, einem Polyoxypropylen-Polyoxyyyathylen-Kondense auf die ADP-induzierte Thromobocytenaggregation in Vitro (The Effect of Pluronic® F-68, a Polyoxypropylene/Polyoxyethylene Condensate, on ADP-Induced Platelet Aggregation in Vitro)," Pflugers Arch., vol. 2, pp. 331-342 (1973).
Benner, et al., "Cold-Induced Platelet Aggregation In Vivo and Its Inhibition by a Nonionic Surface Active Substance," Thrombosis Research, vol. 2, pp. 331-342 (1973).
Hoie, et al., "Effects of Pluronic® F-68, Poloralkol, On Vascular Reistance in Vivo," Journal of Surgical Research, vol. 11, pp. 515-517 (1971).
Hymes, et al., "The Influence of an Industrial Surfactant Pluronic® F-68, In the Treatment of Hemorrhagic Shock," Journal of Surgical Research, vol. 11, pp. 191-197 (1971).
Vasko, et al., "Poloxalkol® (Pluronic® F-68): A Priming Solution for Cardiopulmonary Bypass," Trans. Am. Soc. Artif. Int. Organs, vol. 18, pp. 526-531 (1972).
Rodeheaver, G.T., "Pluronic® F-68: A Promising New Skin Wound Cleanser," Ann Emerg. Med., vol. 9, No. 11, pp. 572-576 (1980).
Rodeheaver, et al., "Mechanical Cleansing of Contaminated Wounds with a Surfactant," J. Biochem. Interactions, vol. 83, pp. 153-1510s (1975).
Kondo, et al., "Prolonged Suspended Animation in Puppies," Cryobiology, vol. 11, No. 5, pp. 446-451 (1974).

Sakauchi, "Prevention of Excess Hemolysis During Cardiopulmonary Bypass by the Use of Pluronic® F-68" *Kitakanto Med. J.*, vol. 23, No. 3, pp. 231-238 (1973).

Hunter et al., "The Adjuvant Activity of Nonionic Block Polymer Surfactants. III. Characterization of Select Biologically Active Surfaces," Scand. J. Immunol. vol. 23, pp. 287-300 (1986).

Michael Simons et al, "Antisense c-*myb* oligonucleotides inhibit intimal arterial smooth muscle cell accumulation in *vivo*," Nature International Weekly Journal of Science, Sep. 3, 1992, pp. 67-70, vol. 359, Japan.

Hunter, et al., "Adjuvant Activity of Non-Ionic Block Copolymers. IV. Effect of Molecular Weight and Formulation on Titre and Isotype of Antibody," Vaccine, vol. 9, pp. 250-256 (1991).

Takayama, et al., "Adjuvant Activity of Non-Ionic Block Copolymers. V. Modulation of Antibody Isotype Lipopolysaccharides, Lipid A and Precursors," Vaccine, vol. 9, pp. 257-265 (1991).

Ketchum, et al., "Experimental Use of Pluronic® F-68 in Microvascular Surgery," *Plastic and Reconstructive Surgery*, vol. 53, pp. 288-292 (1974).

Schmolka, et al., "Artificial Skin I. Preparation and Properties of Pluronic® F-127 Gels for Treatment of Burns," J. Biomed. Mater. Res., vol. 6, pp. 571-582 (1972).

Grover, et al, "A Non-Ionic Surfactant and Blood Viscosity," Arch. Surg. vol. 106, pp. 307-310 (1973).

Grover, et al., "The Effect of Pluronic® F-68 on Circulatory Dynamics and Renal and Carotid Artery Flow During Hemorrhagic Shock," *Journal of Surgical Research*, vol. 17, pp. 30-35 (1974).

Papadea, et al., "Effect of RheothRx™ Copolymer on Blood Viscosity Related to Fibrin (ogen) Concentration," *Faseb J.*, vol. 2, No. 4, pp. A384A, Abstract 512 (1988).

Hunter, et al., "Increased Whole Blood Viscosity During Coronary Bypass Surgery," *Thromb. Haemost.*, vol. 63, No. 1, pp. 6-12 (1990).

Mezrow, et al., "Poloxamer 188 Improves Neurologic Outcome after Hypothermic Circulatory Arrest," *J. Thorac. Cardiovas. Surg.*, vol. 103, No. 6, pp. 1143-1146 (1992).

Nagata, et al., "Clinical Evaluation on the Effect of Poloxamer 188 on the Hemolysis During Cardiopulmonary Bypass," *J. Aichi. Med. Univ. Assoc.*, vol. 11, No. 1, pp. 48-54 (1983).

\* cited by examiner

Selected copolymers are indicated by their CRL designation

Selected copolymers are indicated by their CRL designation

Selected copolymers are indicated by their CRL designation

SEQUENCE LISTING

```
<160> NUMBER OF SEQ ID NOS: 1

<210> SEQ ID NO 1
<211> LENGTH: 14
<212> TYPE: DNA
<213> ORGANISM: Artificial Sequence
```

-continued

```
<220> FEATURE:
<223> OTHER INFORMATION: Synthetic nucleotide

<400> SEQUENCE: 1
tcgtcgctgt ctcg                                               14
```

THERAPEUTIC DELIVERY COMPOSITIONS AND METHODS OF USE THEREOF

The present application is a continuation of U.S. patent application Ser. No. 09/104,088, filed Jun. 24, 1998, abandoned, which is a continuation in part of U.S. patent application Ser. No. 08/926,297, filed Sep. 5, 1997, abandoned, which is a continuation of U.S. patent application Ser. No. 08/725,842, filed Sep. 30, 1996, abandoned, which is a continuation of U.S. patent application Ser. No. 08/138,271, filed Oct. 15, 1993, abandoned.

TECHNICAL FIELD

The present invention relates to therapeutic delivery compounds and to compositions comprising therapeutic delivery compounds that kill or suppress the growth of bacteria, viruses, fungi and protozoa, and methods of use thereof. The compounds, compositions and methods are effective for the delivery of drugs and other compounds to the interior of cells and for controlling intracellular organisms.

BACKGROUND OF THE INVENTION

Many new and potentially useful technologies are being developed which may form the basis of future medical cures and therapies. Examples of such technologies include, gene replacement, antisense gene therapy, triplex gene therapy and ribozyme-based therapy. However, to be successful, these technologies require effective means for the delivery of the therapeutic agent across cellular, nuclear and microorganismal membranes.

The recent advent of technology, and advances in our ability to understand the structure and function of many genes makes it possible to selectively turn off or modify the activity of a given gene. Alteration of gene activity can be accomplished many ways. For example, oligonucleotides that are complementary to certain gene messages or viral sequences, known as "antisense" compounds, have been shown to have an inhibitory effect against viruses. By creating an antisense compound that hybridizes with the targeted RNA message of cells or viruses the translation of the message into protein can be interrupted or prevented. In this fashion gene activity can be modulated.

The ability to deactivate specific genes provides great therapeutic benefits. For example, it is theoretically possible to fight viral diseases with antisense RNA and DNA molecules that seek out and destroy viral gene products. In tissue culture, antisense oligonucleotides have inhibited infections by herpes-viruses, influenza viruses and the human immunodeficiency virus that causes AIDS. It may also be possible to target antisense oligonucleotides against mutated oncogenes. Antisense technology also holds the potential for regulating growth and development. However, in order for the gene therapy to work, antisense therapeutic compounds must be delivered across cellular plasma membranes to the cytosol.

Gene activity is also modified using sense DNA in a technique known as gene therapy. Defective genes are replaced or supplemented by the administration of "good" or normal genes that are not subject to the defect. The administered normal genes which insert into a chromosome, or may be present in extracellular DNA, produce normal RNA, which in turn leads to normal gene product. In this fashion gene defects and deficiencies in the production of gene product may be corrected. Still further gene therapy has the potential to augment the normal genetic complement of a cell. For example, it has been proposed that one way to combat HIV is to introduce into an infected person's T cells a gene that makes the cells resistant to HIV infection. This form of gene therapy is sometimes called "intracellular immunization." Genetic material such as polynucleotides may be administered to a mammal to elicit an immune response against the gene product of the administered nucleic acid sequence. Such gene vaccines elicit an immune response in the following manner. First, the nucleic acid sequence is administered to a human or animal. Next, the administered sequence is expressed to form gene product within the human or animal. The gene product inside the human or animal is recognized as foreign material and the immune system of the human or animal mounts an immunological response against the gene product. However, this approach currently is not feasible due to a lack of effective gene delivery systems that facilitate the delivery of genetic material across both cellular and nuclear membranes.

Finally, gene therapy may be used as a method of delivering drugs in vivo. For example, if genes that code for therapeutic compounds can be delivered to endothelial cells, the gene products would have facilitated access to the blood stream. Currently, genes are delivered to cells ex vivo and then reintroduced to the animal.

Retroviral vectors can be used to deliver genes ex vivo to isolated cells, which are then infused back into the patient. However, retroviral vectors have some drawbacks, such as being able to deliver genes only to dividing cells, random integration of the gene to be delivered, potentially causing unwanted genetic alterations, and possibly reverting back to an infectious wild-type retroviral form. Another drawback of antisense gene therapy is that it is effective at the messenger RNA level, which means that antisense oligonucleotides must be introduced in a quantity to interact with all or a substantial number of the mRNA in the cytosol, and that such treatment is only effective during active synthesis of mRNA. Further, the oligonucleotides must be maintained at this high quantity level throughout mRNA synthesis to be effective over time.

Newly developed "triplex DNA" technology represents an improvement in gene regulation. Triplex DNA technology utilizes oligonucleotides and compounds that specifically bind to particular regions of duplex DNA, thereby inactivating the targeted gene. An advantage of triplex DNA technology is that only a single copy of the oligonucleotide or compound is required to alter gene expression because the binding is at the DNA level, not the mRNA level. A drawback of triplex DNA technology, however, is that the oligonucleotide or compound must pass through not only the cellular membrane, but also the microbial membrane in the case of treating microbial infections, or the nuclear membrane in the case of altering eukaryotic gene function or expression of foreign DNA integrated into chromosomal DNA.

Another emerging technology relates to the therapeutic use of ribozymes for the treatment of genetic disorders. Ribozymes are catalytic RNA molecules that consist of a hybridizing region and an enzymatic region. Ribozymes may in the future be engineered so as to specifically bind to a targeted region of nucleic acid sequence and cut or otherwise enzymatically modify the sequence so as to alter its expression or translation into gene product.

There is a great need, therefore, for improved delivery systems for genetic material such as genes, polynucleotides, and antisense oligonucleotides that can be used in gene therapy. More specifically, there is a need for non-toxic compositions having surfactant properties that can facilitate the transport of genetic compounds and other drugs and therapeutic compounds across cellular membranes.

There is a particularly urgent need for an effective treatment for Acquired Immune Deficiency Syndrome, or AIDS, a disease thought to be caused by a human retrovirus, the Human T Lymphotropic Virus III (HTLV-III) which is also called human immunodeficiency virus or HIV. Like other retroviruses, HIV has ribonucleic acid, or RNA, as its genetic material. When the virus enters the host cell, a viral enzyme called reverse transcriptase exploits the viral RNA as a template to assemble a corresponding molecule of DNA. The DNA travels through the cell nucleus and inserts itself among the host chromosomes, where it provides the basis for viral replication.

In the case of HIV, the host cell is often a T4 lymphocyte, a white blood cell that has a central and regulatory role in the immune system. Once it is inside a T4 cell, the virus may remain latent until the lymphocyte is immunologically stimulated by a secondary infection. Then the virus reproducing itself rapidly killing or rendering ineffective the host cell. The resulting depletion of the T4 cells, and loss of activity leaves the patient vulnerable to "opportunistic" infections by an agent that would not normally harm a healthy person. The virus damages the host by many other mechanisms as well.

Many therapies against AIDS infection that are currently being investigated. Several of these therapies under investigation are based on interrupting the reverse transcriptase as it assembles the viral DNA destined to become the virus. The drugs used for this purpose are chemical analogs of the nucleic acids that form the subunits of DNA. When the analog is supplied to an infected cell, reverse transcriptase will incorporate it into a growing DNA chain. Because the analog lacks the correct attachment point for the next subunit, however, the chain is terminated. The truncated DNA cannot integrate itself into the host chromosomes or provide the basis for viral replication, and so the spread of the infection is halted. One of the compounds that is thought to act by mimicking a nucleotide is azidothymidine, or AZT. However, AZT is known to have serious side effects and its efficacy in mitigating the AIDS disease has been questioned. The efficacy of AZT and other antiviral and antimicrobial drugs could be increased if improved means and methods for delivering therapeutic agents to the site of infection were available.

SUMMARY OF THE INVENTION

The present invention includes a method of delivering therapeutic drugs to a human or animal for treating disease states such as, but not limited to, bacterial infection and infections caused by HIV and other DNA and RNA viruses. The present invention relates particularly to compositions and methods for treating infectious diseases and genetic disorders through gene therapy and intracellular delivery of antisense oligonucleotides or other nucleic acid sequences.

The present invention comprises a therapeutic delivery composition effective for treating a disease state comprising an administerable admixture of an effective amount of a therapeutic compound capable of altering nucleic acid sequence function and an effective amount of a surface active nonionic block copolymer having the following general formula:

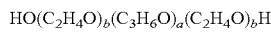

wherein a is an integer such that the hydrophobe represented by ($C_3H_6O$) has a molecular weight of approximately 750 and approximately 15,000, preferably between approximately 2250 and approximately 15,000, more preferably between approximately 3250 and approximately 15,000, and b is an integer such that the hydrophile portion represented by ($C_2H_4O$) constitutes approximately 1% to approximately 50% by weight of the compound, preferably approximately 5% to approximately 20%.

A particularly useful composition is an admixture of a compound capable of altering gene expression and/or protein translation, such as an antisense oligonucleotide, a triplex DNA compound, a ribozyme or other compound capable of altering nucleic acid sequence function, and the above-described nonionic block copolymer.

The composition of the present invention can be administered by a number of routes including, but not limited topical, transdermal, oral, trans-mucosal, subcutaneous injection, intravenous injection, intraperitoneal injection and intramuscular injection.

Accordingly, an object of the invention is to provide a therapeutic drug delivery vehicle.

Another object of the present invention is to provide compositions that facilitate delivery of one or more therapeutic nucleic acid sequence function altering agents into the interior of a cell, such as a phagocytic cell, when admixed with a therapeutic agent.

Another object of the present invention is to provide compositions that act synergistically with a delivered agent once inside a cell.

Still another object of the invention is to provide nonionic block copolymers having surfactant properties that facilitate the transmission and introduction across cellular plasma membranes of nucleic acid sequences and compounds capable of altering nucleic acid sequence function.

A further object of the present invention is to provide compositions and a method for treating genetic and physiologic disorders using nucleic acid sequences and antisense oligonucleotides in combination with nonionic block copolymers.

Another object of the present invention is to provide compositions and a method useful for manipulating the expression of genes using triplex DNA compounds.

Yet another object of the invention is to provide DNA vaccines.

It is an object of the present invention to provide compositions which can be used to treat persons with infectious diseases.

Yet another object of the present invention is to provide a method of treating viral infections in humans or animals.

Another object of the present invention is a compound and method that is effective in inhibiting the replication of viruses in both animals and humans.

Another object of the present invention is to provide a compound and method that is effective in inhibiting the replication of HIV and other RNA and DNA viruses.

Yet another object of the present invention is to provide a method of treating microbial infections in humans or animals.

It is another object of the present invention to inactivate virus in a blood product prior to infusion into a person or animal.

Yet another object of the present invention is to provide compositions that facilitate delivery of one or more therapeutic nucleic acid sequence function altering agents, or nucleic acid sequences into the interior of a cell while increasing the viability of the recipient cells so as to give greater transfection yields.

These and other objects, features and advantages of the present invention will become apparent after a review of the following detailed description of the disclosed embodiment and the appended claims.

DETAILED DESCRIPTION

Figure 1:
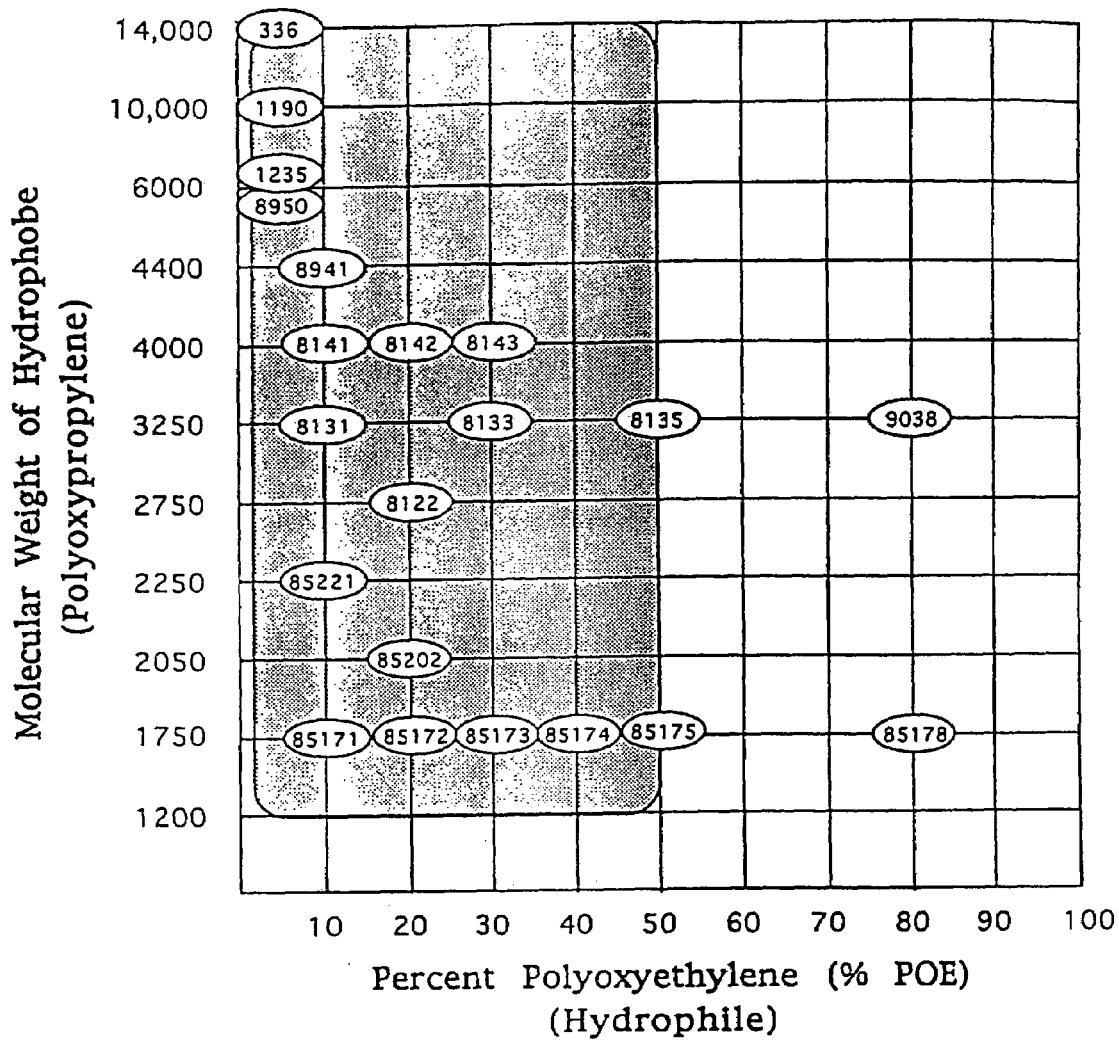
FIG. 1 is a grid illustrating block copolymers by molecular weight of hydrophobe and percent hydrophile.

The present invention includes gene therapy compositions that are admixtures of a nonionic block copolymer and nucleic acid sequences or compounds capable of altering nucleic acid sequence function, and methods of delivering these compositions to a human or animal in need thereof for the intracellular alteration of gene expression and/or protein translation. It has been unexpectedly found that high molecular weight surface active nonionic polyoxyethylene-polyoxypropylene block copolymers having a low percentage of polyoxyethylene facilitate the transport of DNA and other compounds into cells and thus are useful for the intracellular delivery of therapeutic agents in vivo for the treatment of disease. It is believed that the block copolymers are particularly useful in helping to reseal membranes and thus increase the percent survival of cells wherein nucleic acid sequences or other compounds have been intracellularly introduced. Surprisingly, it has also been found that compositions comprising the nonionic block copolymers of the present invention and nucleic acid sequences are less susceptible to the degrading effects of DNAase than nucleic acid sequences alone.

The present invention also comprises therapeutic compositions and methods which kill or inhibit the growth of microorganisms and alter the expression or function nucleic acid sequences. An example of the bacteria that the present invention is effective against is mycobacteria species, such as *Mycobacterium tuberculosis*, *Mycobacterium avium*, and *Mycobacterium leprae*. Other microorganisms that the invention is effective against include, but are not limited to, *Chlamydia trachomatis*, *Chlamydia pneumoniae*, *Listeria monocytogenes*, *Candida albicans*, *Cryptococcus neoformans*, *Toxoplasma gondii*, *Pneumocystis carinii*, Herpes simplex virus type 21, Cytomegalovirus, influenza virus type A and B, and respiratory syncytial virus.

The present invention includes therapeutic compositions and methods for treating DNA viruses and RNA viruses, and infections and infectious diseases caused by such viruses in a human or animal, including infections caused by HIV or herpes or antigenically-related strains thereof. Antigenically-related strains are strains that cross react with antibodies specific for HIV. One skilled in the art can readily determine viral strains that are antigenically-related to HIV by conducting standard immunoassay tests using anti-HIV antibodies and the viral strain to be analyzed, and looking for positive cross-reactivity. The therapeutic compositions comprising the surface active copolymers disclosed herein are effective in inhibiting or suppressing the replication of such viruses in cells.

The present invention includes a therapeutic composition useful for delivering antimicrobial drugs and treating disease states comprising an admixture of a surface active nonionic block copolymer, a compound capable of altering nucleic acid sequence function, and an antibiotic or therapeutic drug. Examples of such compounds capable of altering nucleic acid sequence function include genes, oligonucleotides, antisense oligonucleotides, triplex DNA compounds, and ribozymes. Drugs that can be used with the nonionic copolymers of the present invention include, but are not limited to, rifampin, isoniazid, ethambutol, gentamicin, tetracycline, erythromycin, pyrazinamide, streptomycin, clofazimine, rifabutin, fluoroquinolones such as ofloxacin and sparfloxacin, azithromycin, clarithromycin, dapsone, doxycyline, ciprofloxacin, ampicillin, amphotericin B, fluconazole, ketoconazole, fluconazole, pyrimethamine, sulfadiazine, clindamycin, azithromycin, paromycin, diclazaril, clarithromycin, atovaquone, pentamidine, acyclovir, trifluorouridine, AZT, DDI, DDC, and other antiviral nucleoside analogs, foscornat, ganciclovir, viral protease inhibitors, antisense and other modified oligonucleotides, and ribavirin.

Preferred drugs to use for various infectious microorganisms are listed in Table I.

TABLE I

| Organism | Drugs |
| --- | --- |
| Bacteria | |
| *Mycobacterium tuberculosis* | Isoniazid, rifampin, ethambutol, pyrazinamide, streptomycin, clofazimine, rifabutin, fluoroquinolones such as ofloxacin and sparfloxacin |
| *Mycobacterium avium* | Rifabutin, rifampin, azithromycin, clarithromycin, fluoroquinolones |
| *Mycobacterium leprae* | Dapsone |
| *Chlamydia trachomatis* | Tetracycline, doxycyline, erythromycin, ciprofloxacin |
| *Chlamydia pneumoniae* | Doxycycline, erythromycin |
| *Listeria monocytogenes* | Ampicillin |
| Fungi | |
| *Candida albicans* | Amphotericin B, ketoconazole, fluconazole |
| *Cryptococcus neoformans* | Amphotericin B, ketoconazole, fluconazole |
| Protozoa | |
| *Toxoplasma gondii* | Pyrimethamine, sulfadiazine, clindamycin, azithromycin, clarithromycin, atovaquone |
| *Pneumocystis carinii* | Pentamidine, atovaquone |
| *Cryptosporidium* sp. | Paromomycin, diclazaril |
| Virus | |
| Herpes simplex virus type 1 and type 2 | Acyclovir, trifluorouridine and other antiviral nucleoside analogs, foscornat, antisense oligonucleotides, and triplex-specific DNA sequences |

TABLE I-continued

| Organism | Drugs |
| --- | --- |
| Cytomegalovirus | Foscarnet, ganciclovir |
| HIV | AZT, DDI, DDC, foscarnat, viral protease inhibitors, peptides, antisense oligonucleotides, triplex and other nucleic acid sequences |
| Influenza virus type A and B | Ribavirin |
| Respiratory syncytial virus | Ribavirin |
| *Varizella zoster* virus | Acyclovir |

Optionally, surfactants and low molecular weight alcohols are added to the therapeutic admixture of antimicrobial drug and nonionic block copolymer. Examples of surfactants useful in the present invention include Tween 80 and emulsions with fatty acids such as phospholipids, cholate and amino acids. The preferred surfactant is Tween 80. Surfactants are added to the admixture at a concentration ranging from approximately 0.1% to approximately 5% v/v. The preferred surfactant concentration is approximately 2%. The term "approximately" as it applies to concentrations expressed herein means the stated concentration plus or minus ten percent. The term "low molecular weight alcohols" means alcohols having two to eight carbons. An example of a low molecular weight alcohols useful in the present invention is ethanol, which is the preferred low molecular weight alcohol. Low molecular weight alcohols are added to the admixture at a concentration ranging from approximately 0.5% to approximately 5% v/v. The preferred low molecular weight alcohol concentration is between approximately 1% and approximately 3% v/v.

The present invention also includes compositions and methods for immunizing animals or humans, otherwise termed DNA vaccination. Immunization is accomplished by administering a composition comprising the gene that codes for the gene product to be immunized against contained in an expression, in combination with a block copolymer that promotes and facilitates uptake of genetic material across cell membranes. The introduced gene is expressed, resulting in the production of an antigenic gene product.

Still further, compositions comprising nonionic block copolymers and genes that code for compounds effective for killing, reducing or retarding cancer, such as lymphokines, may be administered to humans or animals for the treatment of cancer.

The present invention comprises a surface active copolymer that is preferably an ethylene oxide-propylene oxide condensation product with the following general formula:

$$HO(C_2H_4O)_b(C_3H_6O)_a(C_2H_4O)_bH$$

wherein a is an integer such that the hydrophobe represented by $(C_3H_6O)$ has a molecular weight of between approximately 750 and approximately 15,000, and b is an integer such that the hydrophile portion represented by $(C_2H_4O)$ constitutes approximately 1% to approximately 50% by weight of the compound.

The present invention also comprises a therapeutic delivery composition useful for altering gene expression and/or protein translation comprising an administerable admixture of an effective amount of an anti-sense oligonucleotide or other nucleic acid sequence, and an effective amount of a nonionic block copolymer having the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 750 and approximately 15,000, preferably between approximately 2250 and approximately 15,000, more preferably between approximately 3250 and approximately 15,000, and b is an integer such that the hydrophile portion represented by $(C_2H_4O)$ constitutes approximately 1% to approximately 50% by weight of the compound, preferably approximately 5% to approximately 20%. The term admixture as used herein means any combination of therapeutic drug and nonionic block copolymer, including solutions, suspensions, or encapsulations of drug in copolymer micelles. An effective amount is an amount sufficient to alter the activity and/or the amount of gene product produced by the gene or genes sought to be modulated in a human or animal.

The present invention also comprises a therapeutic delivery composition useful for immunizing an animal or human against a particular gene product comprising an administerable admixture of an effective amount of an expression vector, the gene that codes for the gene product to be immunized against contained in the expression vector, and an effective amount of a nonionic block copolymer having the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 750 and approximately 15,000, preferably between approximately 2250 and approximately 15,000, more preferably between approximately 3250 and approximately 15,000, and b is an integer such that the hydrophile portion represented by $(C_2H_4O)$ constitutes approximately 1% to approximately 50% by weight of the compound, preferably approximately 5% to approximately 20%. An effective amount is an amount sufficient to elicit an immunological response against the gene product of the nucleic acid sequence administered to the human or animal.

It should be understood that the molecular weight and percentage ranges that are described for the block copolymer are to be considered outside ranges and that any population of molecules that falls within the stated ranges is considered an embodiment of the present invention.

The entire block copolymer molecule is poorly soluble in water and is substantially nonionic. The steric configurations and physiochemical properties of the molecule, rather than the chemical nature of the constituent parts, are believed to be largely responsible for the antiinfective activity and therapeutic delivery activity. Compositions of the present invention include, but are not limited to aqueous solutions, suspensions or emulsions, such as oil-in-water emulsions.

The polymer blocks are formed by condensation of ethylene oxide and propylene oxide, at elevated temperature and pressure, in the presence of a catalyst. There is some statistical variation in the number of monomer units which combine to form a polymer chain in each copolymer. The molecular weights given are approximations of the average weight of copolymer molecule in each preparation and are dependent on the assay methodology and calibration standards used. It is to be understood that the blocks of propylene oxide and ethylene oxide do not have to be pure. Small amounts of other materials can be admixed so long as the overall physical chemical properties are not substantially changed. A more detailed discussion of the preparation of these products is found in U.S. Pat. No. 2,674,619, which is incorporated herein by reference in its entirety.

Ethylene oxide-propylene oxide condensation products which may be employed in the present invention are summarized in Table II. It is to be understood that these compounds are merely representative of the compounds that can be used to practice the present invention and do not include all possible compounds that could be used to practice the present invention. The high molecular weight copolymers listed in Table II that do not have a BASF tradename are novel compositions that have never been synthesized before.

TABLE II

| CRL # | Poloxamer | BASF Trade Name | Molecular Weight of POP | % POE |
|---|---|---|---|---|
| | 122 | L42 | ≈1200 | ≈20% |
| CRL-85171 | 181 | L61 | ≈1750 | ≈10% |
| CRL-85172 | 182 | L62 | ≈1750 | ≈20% |
| CRL-85173 | 183 | L63 | ≈1750 | ≈30% |
| CRL-85174 | 184 | L64 | ≈1750 | ≈40% |
| CRL-85175 | 185 | P65 | ≈1750 | ≈50% |
| CRL-85178 | 188 | F68 | ≈1750 | ≈80% |
| CRL-85202 | 212 | L72 | ≈2050 | ≈20% |
| CRL-85221 | 231 | L81 | ≈2250 | ≈10% |
| CRL-8122 | 282 | L92 | ≈2750 | ≈20% |
| CRL-8131 | 331 | L101 | ≈3250 | ≈10% |
| CRL-8133 | 333 | P103 | ≈3250 | ≈30% |
| CRL-8135 | 335 | P105 | ≈3250 | ≈50% |
| CRL-9038 | 338 | F108 | ≈3250 | ≈80% |
| CRL-8141 | 401 | L121 | ≈4000 | ≈10% |
| CRL-8142 | 402 | L122 | ≈4000 | ≈20% |
| CRL-8143 | 403 | P123 | ≈4000 | ≈30% |
| CRL-8941 | 441 | L141 | ≈4400 | ≈10% |
| CRL-8950 | — | — | ≈6000 | ≈5% |
| CRL-1235 | — | — | ≈7500 | ≈5% |
| CRL-1190 | — | — | ≈10,000 | ≈5% |
| CRL-336 | — | — | ≈14,000 | ≈5% |
| CRL-1183 | — | — | ≈3750 | ≈10% |
| CRL-1122 | — | — | ≈5900 | ≈12% |
| CRL-3362 | — | — | ≈3900 | ≈11% |
| CRL-3632 | — | — | ≈4740 | ≈11% |
| CRL-9352 | — | — | ≈7750 | ≈15% |
| CRL-1187 | — | — | ≈750 | ≈25% |

A grid illustrating the range of copolymer encompassed by the present invention based upon the molecular weight of the hydrophobe portion and the percent hydrophile, and showing selected nonionic block copolymers appears as FIG. 1. The polymer blocks are formed by condensation, at elevated temperature and pressure, of ethylene oxide and propylene oxide in the presence of a catalyst. There is some statistical variation in the number of monomer units which combine to form a polymer chain in each copolymer. The molecular weights given are approximations of the average size of copolymer molecules in each preparation. A further description of the preparation of these block copolymers is found in U.S. Pat. No. 2,674,619. (Also see, "A Review of Block Polymer Surfactants", Schmolka I. R., *J. Am. Oil Chemist Soc.*, 54:110–116 (1977) and *Block and Graft Copolymerization*, Volume 2, edited by R. J. Ceresa, John Wiley and Sons, New York, 1976.

Figure 2:
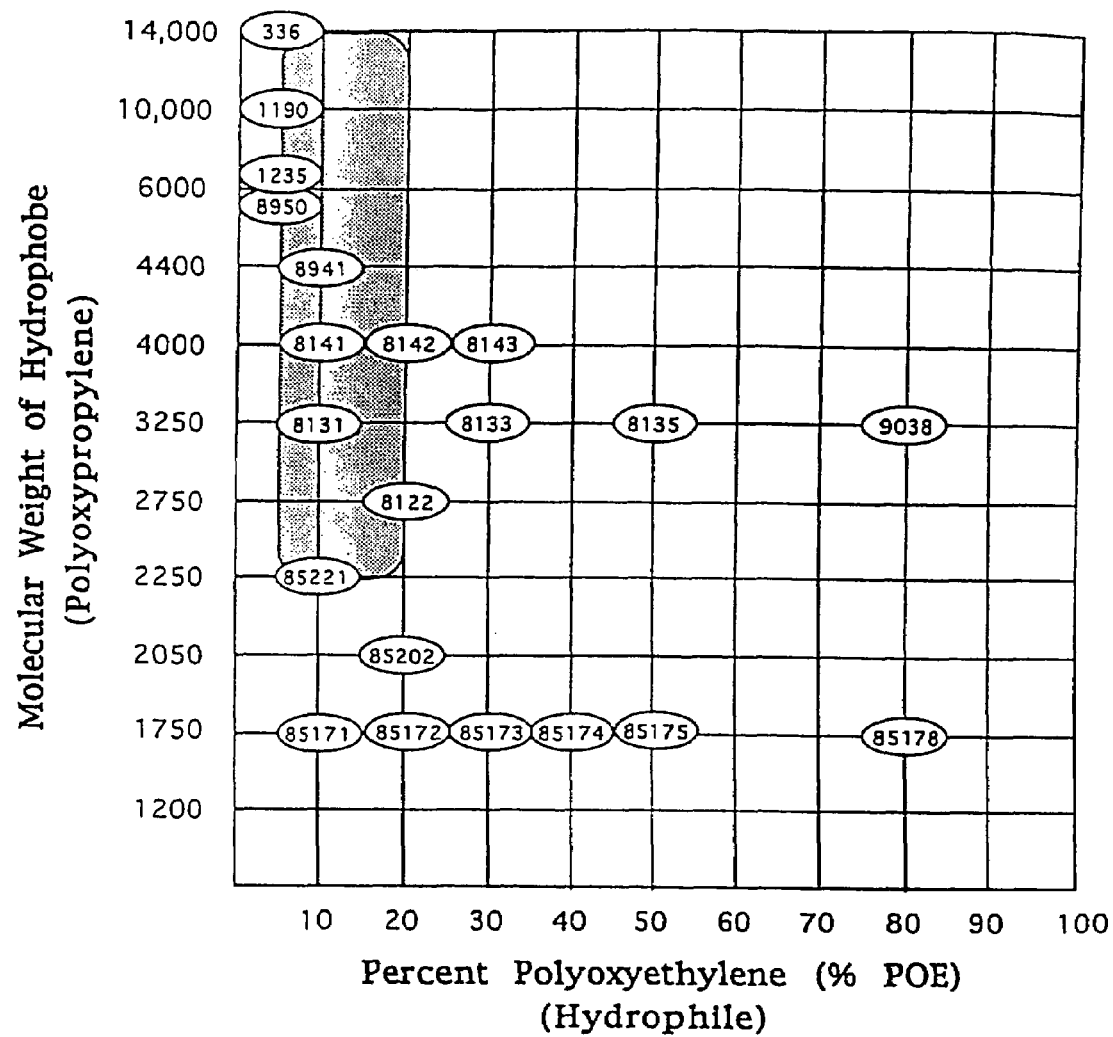
FIG. 2 is a grid illustrating preferred therapeutic delivery block copolymers by molecular weight of hydrophobe and percent hydrophile.
Figure 3:
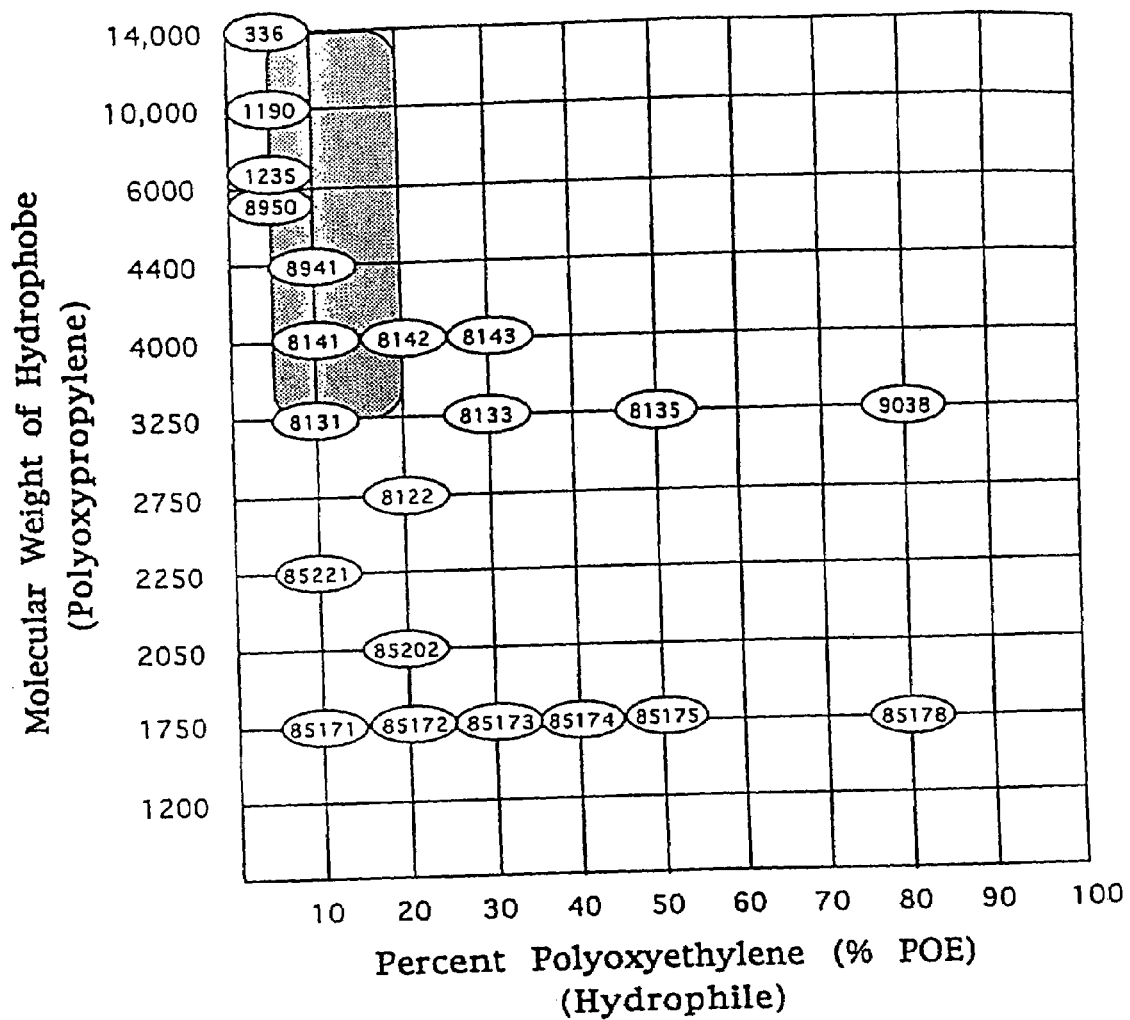
FIG. 3 is a grid illustrating more preferred therapeutic delivery block copolymers by molecular weight of hydrophobe and percent hydrophile.
Figure 4:
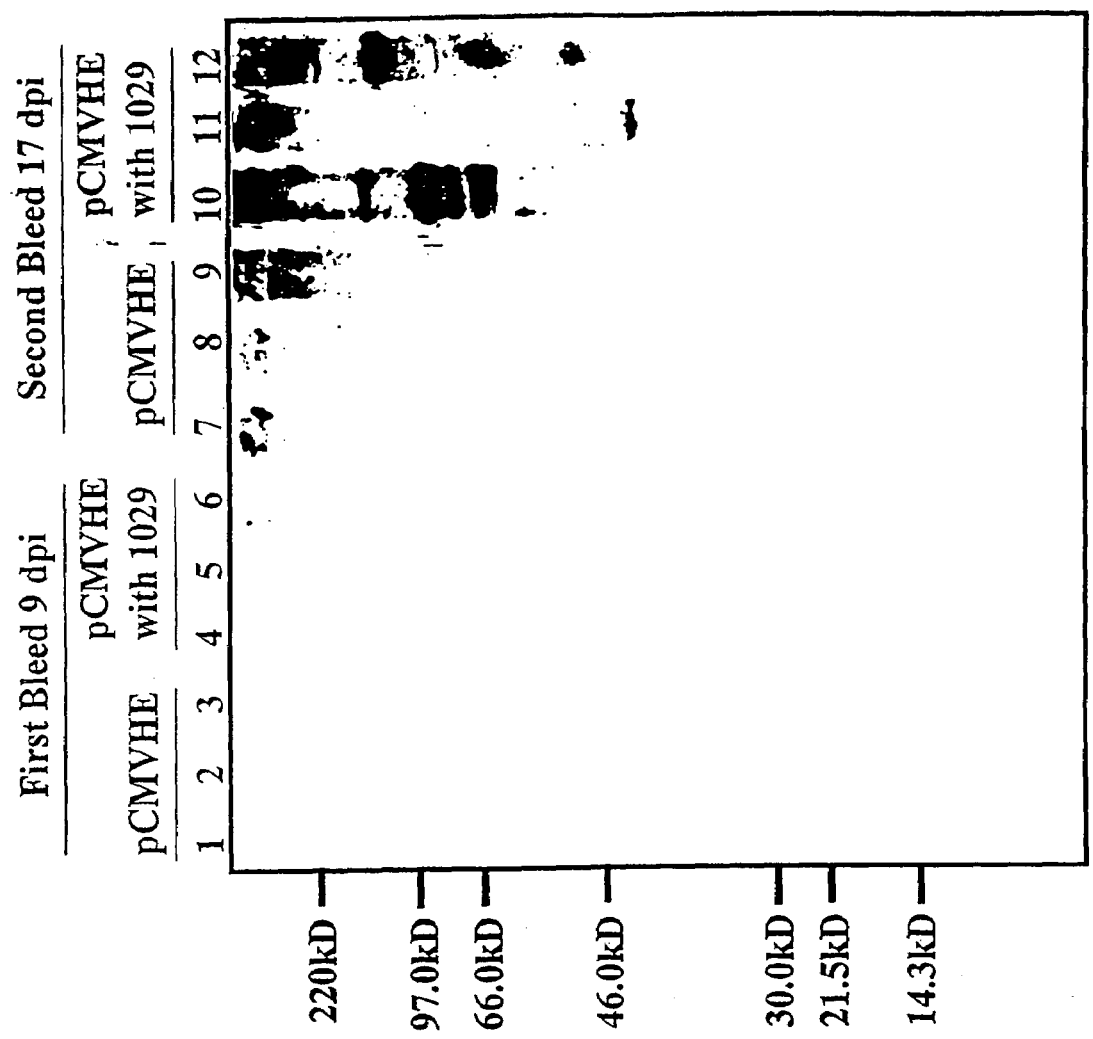
FIG. 4 is a Western blot analysis showing that poloxamer 1029 increases the level of anti-HE antibody production. The photograph shows the chemiluminescent trace after exposure of the filter to the Supersignal™ system.

It has been discovered that the copolymers particularly effective as therapeutic delivery agents are shown in FIGS. 2 and 3. As is apparent from FIGS. 2 and 3, the copolymers most effective as therapeutic delivery agents are high molecular weight and have low percentages of POE—generally less than 20% POE. Effective percentages may extend to approximately 25%. Another preferred mode of administration is by intramuscular injection.

Non-ionic block copolymers form micelles above their critical micelle concentration. The non-ionic copolymers have negative thermal coefficients of solubility. In the cold, the kinetic energy of water molecules is reduced and they form weak hydrogen bonds with the oxygen of the POP blocks. This hydration of the hydrophobe promotes solubility at low temperatures. As the temperature rises, the "cloud point" is reached; the increased kinetic energy of the water breaks the hydrogen bonds, the polymer becomes insoluble and micelles form.

Thus, the copolymers, which are therapeutic themselves, can form physical structures that can be combined or loaded with an additional, distinct therapeutic agent. Consequently, the nonionic block copolymers of the present invention can be used as therapeutic drug delivery vehicles. Admixtures of therapeutic drugs with non-ionic block copolymers have the advantage of synergistic activity of two therapeutic agents. Further, copolymers having specific characteristics can be selected for use with particular therapeutic drugs. For example, CRL-8131, which is hydrophobic, is an excellent carrier for hydrophobic antibiotics such as rifampin. However, other agents which are not distinctly hydrophobic can be used according to the present invention.

A therapeutic delivery vehicle is prepared using any of the surface active nonionic block copolymers of the present invention in combination with any of a variety of antimicrobial agents. In a one embodiment CRL-8131 is used at a concentration of approximately 3% to approximately 5% to construct a therapeutic delivery vehicle. Therapeutic delivery vehicles made using copolymers that are more hydrophilic than CRL-8131 normally require a higher concentration (approximately 5% to approximately 10%) of the copolymer.

Using copolymer-based micelles as a therapeutic drug delivery vehicle is particularly desirable because the micelles are accumulated readily and are present for an extended period of time, in macrophages, the site of HIV and other viral infections and a major target for viral therapy. Examples of such therapeutic copolymer-based therapeutic compositions include CRL-8131 combined with 2% Tween 80 and 1% ethanol, and CRL-8142 combined with 1% Tween 80 and 5% ethanol.

Nucleic acid sequences or other compounds capable of altering nucleic acid sequence function are administered to a human or animal to alter gene expression and/or modify the amount or activity of gene product. For example, antisense oligonucleotides admixed with the above-described nonionic block copolymers yield compositions useful for delivery of the antisense oligonucleotides for the purpose of altering or regulating gene expression and/or protein translation. Further, nucleic acid sequences such as genes can be administered which incorporate into the chromosome replacing or augmenting the defective gene. Alternatively, the intracellularly administered gene may reside in the cell and be expressed in an extrachromosomal element.

The present invention also provides novel compositions and methods for immunizing an animal or human. The compositions comprise an expression vector, a gene that codes for the gene product to be immunized against contained in the expression vector, and a block copolymer effective for transferring genetic material such as expression vectors across the membrane of cells. The method of immunizing an animal or human comprises administering of the expression vector-containing copolymer composition to the animal or human. A preferred mode of administration is by intraperitoneal injection. This embodiment of the invention provides means for the delivery of genetic sequences capable of expressing an antigenic gene product directly into human or animal cells, either in vivo or ex vivo with subsequent reintroduction into the human or animal. Once introduced into the cells the production of antigenic gene product induces and maintains an immune response by the human or animal against the introduced gene product.

The following specific examples illustrate various aspects of the invention, such as compositions and methods of the invention useful for gene therapy, and compositions and methods of the invention useful for gene-mediated immunization. It should be appreciated that other embodiments and uses will be apparent to those skilled in the art and that the invention is not limited to these specific illustrative examples.

EXAMPLE I

A therapeutic delivery vehicle is prepared by combining any of the surface active nonionic block copolymers, such as CRL-8131 with any of a variety of compounds capable of altering nucleic acid sequence function. For CRL-81312 a concentration of three to five percent weight per volume is desirable to construct the therapeutic vehicle. For more hydrophilic copolymer a five to ten percent weight per volume.

300 milligrams of CRL-8131 was added to 10 ml of 0.9% NaCl and the mixture is solubilized by storage at temperatures of 2–4° C. until a clear solution is formed. An appropriate amount of a compound capable of altering nucleic acid gene function is added to the mixture and micelles associating the copolymer and the compound are formed by raising the temperature above 5° C. and allowing the suspension of micelles to equilibrate. The equilibrated suspension is suitable for administration.

For example, an antisense oligonucleotide sequence, such as one of those disclosed by Matsukara, M. et al. *Proc. Natl. Acad. Sci. USA* 84:7706–7710 (1987), which is expressly incorporated herein in its entirety by reference, is combined with the copolymer to form a micelle composition.

Briefly, phosphorothioate or methylphosphonate derivatives of a sequence complimentary to regions of the art/trs genes of HIV having the sequence 5'-TCGTCGCT-GTCTCG-3' (SEQ ID NO: 1) are prepared according to the method of Matsukura et al. Three hundred milligrams (300 mg) of CRL-8131 is added to 10 ml of 0.9% NaCl and the mixture is solubilized by storage at temperatures of 2–4° C., until a clear solution is formed. The desired antisense oligonucleotide subsequently is mixed with the copolymer solution to provide a concentration effective in inhibiting viral activity when administered to a patient infected with the HIV virus. Generally the effective amount of antisense compound will be such that the final concentration in the blood is in the range of 1 µM to 100 µM, although other effective amounts of antisense compounds outside this range may be found for specific antisense compounds. One skilled in the art can readily test the relative effectiveness of any particular antisense oligonucleotide according to the in vivo test of Matsukura et al.

An average person has approximately 6.25 liters of blood. Thus, oligonucleotide concentrations of approximately 6 mM to 600 mM are required in the composition when 1 ml injections are to be administered. Lower oligonucleotide compositions can be used with larger administration volumes.

EXAMPLE II

The antiinfective antisense oligonucleotide composition of Example I is administered to HIV patients by any route effective to reduce viral activity. The preferred route of administration is by intravenous injection. The antisense composition may be administered multiple times a day to ensure that an effective amount of the antisense oligonucleotide is maintained.

EXAMPLE III

A gene therapy composition for treating an animal or human suffering from the effects of a defective or missing gene is made by combining a copolymer, such as CRL-8131 with a normal copy of the defective gene. For example, for patients suffering from adenosine deaminase (ADA) deficiency a gene therapy composition is made that contains a normal copy of the adenosine deaminase gene. The gene therapy composition is made by mixing a copolymer prepared as described above in Example I with the desired gene, removing blood from the human or animal, transfecting blood cells with the ADA gene-containing composition, and reintroducing the transfected blood cells into the human or animal. The introduced gene is expressed in vivo, alleviating the effects of the original gene deficiency.

EXAMPLE IV

Similarly, the gene therapy composition of Example III is combined with isolated T-lymphocytes to form T-lymphocytes containing the ADA gene. The ADA gene-containing T-lymphocytes are subsequently administered, for example by injection, into the patient suffering from adenosine deaminase deficiency. The administered cells express the ADA and produce adenosine deaminase, thus augmenting the supply of the enzyme in the patient and correcting the deficiency.

EXAMPLE V

DNA vaccination is carried out essentially as described for gene therapy in Examples III or IV, except that the gene that is introduced into the host expresses an antigenic gene product that is recognized as foreign by the host animal, thus eliciting an immune response.

EXAMPLE VI

A composition comprising copolymer CRL-8131 and an expression vector containing the gD gene of Herpes simplex virus type-1 was used in a transfection experiment. DNA transfection normally is performed using standard calcium chloride and DEAE dextran precipitation techniques. DEAE dextran is used to rough up the cell membrane and calcium is used to precipitate DNA onto the cell surface, facilitating DNA uptake into the cells. This procedure is generally toxic to the cells, however, and causes substantial cellular mortality.

A new transfection system was discovered using the block copolymer of the present invention in place of calcium chloride. In fact, it was surprisingly discovered that copolymer assisted transfection occurs even in the absence of DEAE dextran.

Vero cells were incubated in DEAE dextran for 30 seconds. A mixture of copolymer and an expression vector containing glycoprotein gD DNA of Herpes simplex virus type-1 was added to Vero cells immediately after the removal of DEAE dextran. It was found that up to 40% of the cells were effectively transfected with the gD gene.

Surprisingly, in two out of four experiments copolymers were able to transfect Vero cells at a lower than 40% efficiency even when the DEAE dextran incubation step is omitted.

EXAMPLE VII

Other studies have also demonstrated that block copolymers are effective in transferring genetic material across cellular membranes in vivo. DNA vaccine-induced immunization was successful when an expression vector containing the gD gene of Herpes simplex virus type-1 combined with copolymer was injected intraperitoneally into rabbits every two weeks. Sera was collected and tested for the presence of anti-gD antibody. Low levels of anti-gD antibody were detected after 4 weeks of inoculation in this fashion. These results demonstrate that genetic material administered intraperitoneally with a copolymer delivery vehicle is taken up by cells in vivo and expressed to give the gene product in quantities sufficient to elicit an immune response.

EXAMPLE VIII

DNAse protection experiments. Five different compounds (CRL 1122, 3362, 3632, 9352, and 8131) were used in experiments to test the degree of protection. DNA was mixed with compounds at 4° C., and after 15 min. at 37° C. DNAse I (1 µl of 10 mg/ml solution) was added. After 30 min. of incubation at 37° C., DNAse I was removed by treatment with proteinase K (3 µl of 10 mg/ml solution). Controls were: DNAse I in the absence of nonionic block copolymer and DNA alone without any DNAse I treatment.

DNA was protected from DNAse I degradation in all samples in which nonionic block copolymers were present. The best protection of DNA was achieved with CRL-3362 and 8131. DNA copolymer compositions did not migrate in horizontal agarose electrophoresis and remained within the wells (stained with ethidium bromide). Effective protection against DNAse I action was achieved in solutions of 1 volume DNA solution (1 µg/ml) to 5 volumes of nonionic block copolymer (30 µg/ml). The estimated amount of protection varied from experiment to experiment and was estimated to be within 15–40% of total DNA.

Additional experiments showed that DNA-copolymer compounds failed to transform *E. coli* competent cells via the calcium method. Phenol also failed to dissolve nonionic block copolymer away from DNA. DNA bound to NBC can be precipitated by adding 5 volumes of isopropyl alcohol.

EXAMPLE IX

Transfection experiments. Typical transfection experiments for transient expression of herpes viral glycoprotein genes and other genes of interest involved the following procedure. Cells such as COS (African monkey kidney cells; CV1) are seeded on 6-well plates. Transfection is performed when cells are 50–80% confluent (still in log growth phase). Cells are first washed with PBS buffer, they are incubated with 0.5 ml of DEAE-Dextran solution (500 mg/ml) for 1–2 minutes, this solution is aspirated and DNA precipitate is added to cells. DNA to be transfected is mixed for 30 min. at room temperature with $CaCl_2$ at controlled pH conditions to form a fine precipitate. This solution is mixed with 1 ml of growth medium (DMEM) and put onto cells for 4 hours at 37° C. At this time, the cells are shocked with 15% glycerol and subsequently washed with PBS. This osmotic shock facilitates the taking up of $CaCl_2$-DNA precipitate into cells. Cells are then washed again with PBS, and incubated with growth media at 37° C. for 48 hours.

Gene expression is detected in most cases using specific monoclonal antibodies directed against the expressed proteins using indirect immunofluorescence. The expressed proteins can be also labeled with radioactive tracers and immunoprecipitated or detected in westerns.

25 µl of DNA (7 µg) and 25 µl of nonionic block copolymer (30 µg/ml) were used. Additionally, mixing of nonionic block copolymer with DNA on ice, and addition of mixture into the cells produced similar results as when they were added separately (DNA added first and nonionic block copolymer second).

Copolymers 1183, 1187, 8131, 1235, 8950AQ and 1190AQ (where AQ indicates that the nonionic block copolymers were diluted 1:10 and 25 µl were used). Typical results are as follows. Transfection with DNA alone, dextran alone, copolymer alone, and DNA plus dextran had negligible transfection of less than 0.2%. In contrast, the positive control of DNA plus dextran plus glycerol has transfection of 2% while various copolymers plus DNA were successful in transfecting DNA into cells up to 2.5 times better than the control, as shown in Table III:

TABLE III

| Copolymer | Percent Transfection |
| --- | --- |
| 1183 | 2% |
| 1187 | 5% |
| 8131 | 2% |
| 1235 | 3% |
| 8950 AQ | 4% |
| 1190 AQ | 5% |

There was no copolymer associated toxicity except mild toxicity with 1187. The others were toxic especially after glycerol treatment.

EXAMPLE X

The presence of copolymer with transfecting DNA increased the yield of transfectants. Trypsinized COS cells were plated at a density of $3 \times 10^5$ with Iscove's Modified Essential Media (IMDM) and 10% fetal bovine serum and incubated to 70–80% confluency. The cells were washed and covered with IMDM without the serum. 3.3 µg β-galactosidase encoding DNA was mixed with 333 µl IMDM and kept at 0°. 10 µl of a 1% copolymer solution was mixed with 333 µl IMDM at 0°. The β-galactosidase and the copolymer solutions were mixed and the entire volume added to a plate of cells. After incubating at 37° for 16 hrs fresh medium with fetal bovine serum was added for 18–24 hrs. The cells were then fixed with 1.5 ml 2% paraformaldehyde, washed and covered with a solution of X-gal overnight. Cells transfected with the b-galactosidase gene stained blue.

Figure 5:
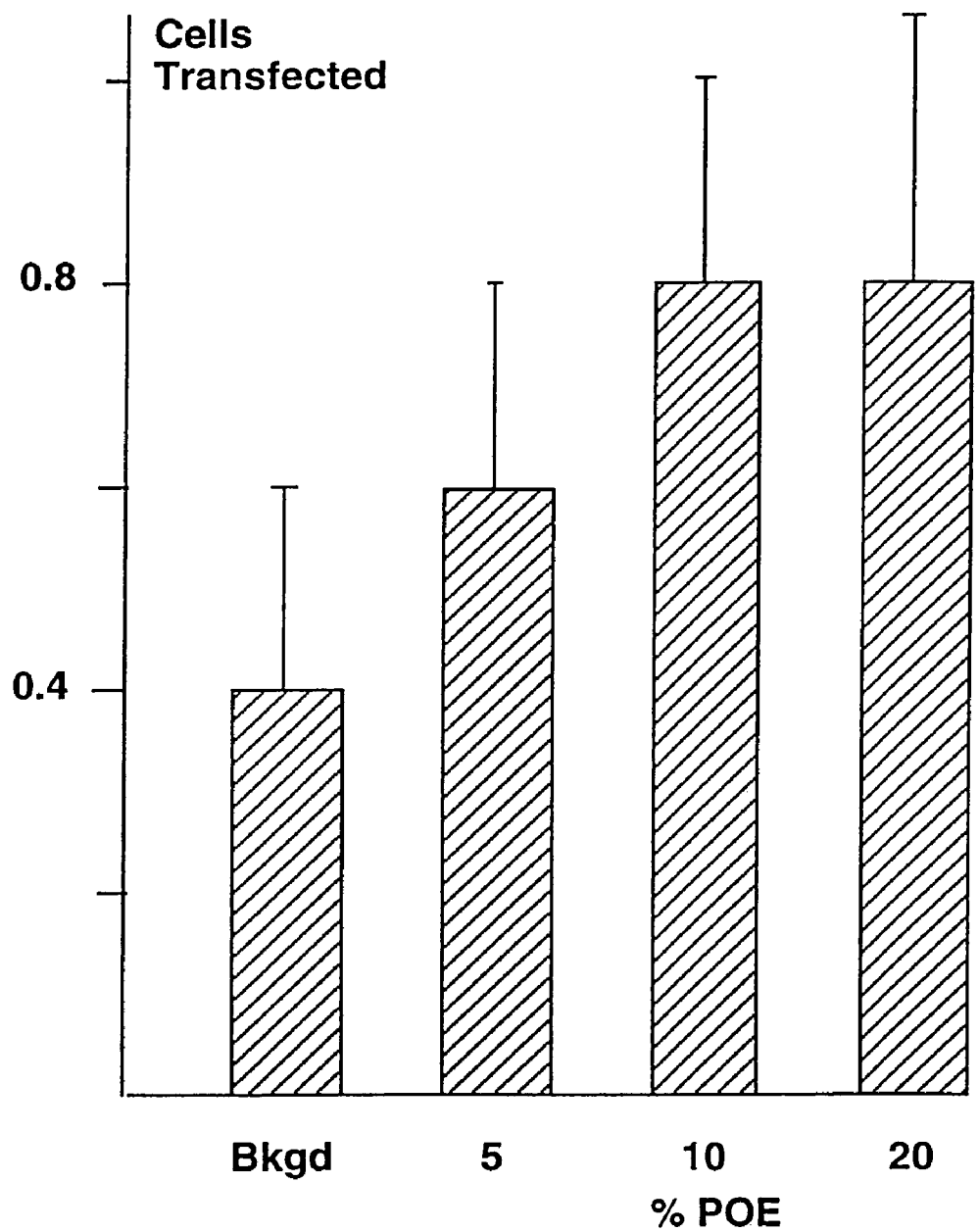
FIG. 5 is a graph showing the increase in the yield of transfected cells as a function of the presence, and the proportion, of the POE, of a copolymer added to the transfection of COS cells by β-galactosidase-encoding DNA. The transfectant yield is given as the number of blue cells per x500 microscope field. The copolymers used were: 5% POE, CRL8623; 10% POE, CRL1415; 20% POE, CRL2022.

FIG. 5 clearly shows that the presence of the copolymer increases the yield of the cells receiving the transfected DNA. The increase in the yield with an increase in the proportion of POE in a copolymer is also readily seen.

EXAMPLE XI

Inclusion of a copolymer increased the viability of cells in transfection experiments. Copolymer CRL1018 increased the viability of transfected cells up to 39%. CRL2022 gave up to a 5% increase, as shown in Table IV. The commercial transfecting agent Transfectam, on the other hand, decreased the viability of the transfected cells by as much as 15.3% (Table IV). Plasmid DNA alone had no effect on recipient cell viability.

The viability was measured by the WSI-vital dye system, a method well known to one skilled in the art. This assay measures the viability of the cells by the degree of dye uptake by the cells and subsequent metabolism. The higher numeric values indicated a greater percentage of surviving cells. The increased viability of the cells in the presence of copolymer allowed a longer effective period for living cells to be in contact with the transfecting agent, and resulted in the DNA uptake by more live cells. This resulted in a higher yield of transfectants.

EXAMPLE XII

Antibodies were induced by protein expression in vivo following the inoculation of mice with DNA in combination with copolymers of the present invention. A cDNA encoding the hemagglutinin-esterase (HE) glycoprotein of the bovine coronavirus was amplified from viral RNA by RT-PCR. The DNA was cloned into the plasmid vector pCR™II (In Vitrogen, Inc.), and then into the expression plasmid pCNDA 3.1/zeo(+), (In Vitrogen, Inc.) to create plasmid pcDNA/HE.

About 0.075 mg/ml of pcDNA/HE in phosphate buffered saline (PBS) was mixed with 0.5 mg/ml of copolymer 1029 (Mol W 12000, 5% POE) in an ice-bath, and kept cold until the mixture became clear. Then the mixture was shifted to room temperature until a cloudy suspension was observed. This process was repeated three times, and then one-third of the 1 ml mixture was introduced intramuscularly into each of three mice. The same amount of plasmid in PBS, but without copolymer 1029, was similarly injected intramuscularly into three different mice. Animals were boosted every two weeks, bled one day prior to each boost and after the fourth injection. Mice sera were then tested for the presence of anti-HE antibodies by Western blotting.

Human rectal tumor cells (HRT-18G) were infected with bovine coronavirus. Proteins were extracted with 1% Novidet P-40 and 0.5% sodium deoxycholate. Aliquots were subject to SDS-gel electrophoresis, and Western blotted to a nitrocellulose filter. The filter sheet was divided into separate lanes, and each lane screened with the Supersignal Substrate Western Blotting kit according to the manufacturer's instructions (Pierce, Inc., Rockford, Ill.). The primary antibody for the screenings were the serum samples from the immunized mice. Serum samples were diluted 1:100 for testing. The result is shown in FIG. 4.

FIG. 4 clearly shows an elevated signal with sera from mice injected with plasmid and copolymer 1029, after 17 days (lanes 10–12), when compared with the sera from mice injected solely with plasmid (lanes 7–9). This result demonstrated the positive adjuvant effect of the copolymer 1029, i.e. the elevation of the immune response induced by intramuscular inoculation of DNA encoding the antigen.

EXAMPLE XIII

The effectiveness of the copolymers to increase the production of antibodies and simultaneously protect whole 'hairless' strain mice against a viral attack was shown when mice were intramuscularly inoculated with plasmid pcDNA carrying a DNA fragment encoding the gB or gD genes of the Herpes simplex virus (HSV). The inocula were plasmid alone, or plasmid together with either copolymer 1029 or 1190. Animals were boosted at 3–4 week intervals, bled for serum for analysis of anti-gD or anti-gD antibodies, and challenged with $2.5\times10^4$ pfu of HSV.

All control animals that received no plasmid and no copolymer died when challenged with virus. When the copolymers were included in the inocula all of the infected animals survived. Humoral antibody production directed against gB and gD protein was also significantly stimulated when the copolymers were included with the plasmid inocula. The copolymers provided increased protection against subsequent viral infection.

TABLE IV

| SAMPLE | ADJUVANT | VIABILITY | % CHANGE |
|---|---|---|---|
| Cells | — | 0.391 | — |
| Cells & plasmid | — | 0.388 | −1.0% |
| Cells | Transfectam | 0.340 | −13.0% |
| Cells + plasmid | Transfectam | 0.331 | −15.3% |
| Cells | CRL 1018 (10 μg) | 0.509 | +30.2% |
| Cells | CRL 1018 (100 μg) | 0.540 | +38.1% |
| Cells | CRL 1018 (1 mg) | 0.545 | +39.3% |
| Cells | CRL 2022 (10 μg) | 0.411 | +5.0% |
| Cells | CRL 2022 (100 μg) | 0.407 | +4.1% |
| Cells | CRL 2022 (1 mg) | 0.411 | +5.0% |

The change in the viability of the cells was measured as the change in the number of cells still alive after exposure to the copolymer when compared to untreated cells.

The copolymers increased the viability of the cellsby 5–39% depending upon the copolymer used. The viability of cells was reduced by 15.3% when mixed with Transfectam. Since cells transfected in the presence of the copolymers survived for a longer period than did those cells either untreated or treated with Transfectam, the survivors would be exposed to the transfecting agent for prolonged periods, giving greater yields of the transfectants.

It should be understood that the foregoing relates only to preferred embodiments of the present invention and that numerous modifications and alterations may be made without departing from the spirit and scope of the invention as set forth in the appended claims.

We claim:

1. A composition comprising, a nonionic block copolymer, wherein the block copolymer has the following formula:

$$HO(C_2H_4O)_b(C_3H_6O)_a(C_2H_4O)_bH$$

wherein "a" is a number such that the molecular weight of the hydrophobe $(C_3H_6O)_a$, represented by the polyoxypropylene portion of the copolymer, is between approximately 750 and 15,000 Daltons; and "b" is a number such that the hydrophile $(C_2H_4O)_b$ portions of the block copolymer, represented by the polyoxyethylene portions of the block copolymer, together are approximately 1% to approximately 50% of the total weight of the block copolymer, and
   one or more nucleic acid molecules selected from the group consisting of: oligonucleotides, antisense oligonucleotides, triplex DNA compounds, ribozymes, and mixtures thereof;
   wherein the composition further comprises an antimicrobial drug selected from the group consisting of; rifampin, isoniazid, ethambutol, gentamicin, tetracycline, erythromycin, pyrazinamide, streptomycin, clofazimine, rifabutin, fluoroquninolones, azithromycin, clarithromycin, dapsone, doxycyline, ciprofloxacin, ampicillin, amphotericin B, fluconazole, ketoconazole, pyrimethamine, sulfadiazine, clindamycin, paromycin, diclazaril, atovaquone, pentamidine, acyclovir, trifluorouridine, AZT, DDI, DDC, forscarnet, viral protease inhibitors, ganciclovir, ribavirn, antiviral nucleoside analogs, and a combination thereof.

2. A method of delivering a molecule to an animal, comprising administering to the animal a composition comprising a nonionic block copolymer, wherein the block copolymer has the following formula:

$$HO(C_2H_4O)_b(C_3H_6O)_a(C_2H_4O)_bH$$

wherein "a" is a number such that the molecular weight of the hydrophobe $(C_3H_6O)_a$, represented by the polyoxypropylene portion of the copolymer, is between approximately 750 and 15,000 Daltons; and "b" is a number such that the hydrophile $(C_2H_4O)_b$ portions of the block copolymer, represented by the polyoxyethylene portions of the block copolymer, together are approximately 1% to approximately 50% of the total weight of the block copolymer,
   wherein the nonionic block copolymer facilitates entry of the molecule into a cell, and
   one or more nucleic acid molecules selected from the group consisting of: oligonucleotides, antisense oligonucleotides, triplex DNA compounds, ribozymes, and mixtures thereof;
   wherein the one or more nucleic acid molecules are used for hybridization with one or more targeted RNA messages of a cell or virus.

3. A method of delivering a molecule to an animal, comprising administering to the animal a composition comprising a nonionic block copolymer, wherein the block copolymer has the following formula:

$$HO(C_2H_4O)_b(C_3H_6O)_a(C_2H_4O)_bH$$

wherein "a" is a number such that the molecular weight of the hydrophobe $(C_3H_6O)_a$, represented by the polyoxypropylene portion of the copolymer, is between approximately 750 and 15,000 Daltons; and "b" is a number such that the hydrophile $(C_2H_4O)_b$ portions of the block copolymer, represented by the polyoxyethylene portions of the block copolymer, together are approximately 1% to approximately 50% of the total weight of the block copolymer,
   wherein the nonionic block copolymer facilitates entry of the molecule into a cell, and
   one or more nucleic acid molecules selected from the group consisting of: genes, oligonucleotides, antisense oligonucleotides, triplex DNA compounds, ribozymes, and mixtures thereof;
   wherein one or more of the nucleic acid molecules is a gene used for supplying to an animal with a defective copy of one of its genes a normal copy of that gene; and,
   wherein one or more of the nucleic acid molecules encodes a normal copy of the gene.

4. A method for immunizing an animal against a particular gene product comprising administering to an animal a composition comprising a nonionic block copolymer, wherein the block copolymer has the following formula:

$$HO(C_2H_4O)_b(C_3H_6O)_a(C_2H_4O)_bH$$

wherein "a" is a number such that the molecular weight of the hydrophobe $(C_3H_6O)_a$, represented by the polyoxypropylene portion of the copolymer, is between approximately 750 and 15,000 Daltons; and "b" is a number such that the hydrophile $(C_2H_4O)_b$ portions of the block copolymer, represented by the polyoxyethylene portions of the block copolymer, together are approximately 1% to approximately 50% of the total weight of the block copolymer,
   an expression vector, wherein the expression vector contains a gene that codes for the gene product to be immunized against;
   and wherein the composition further comprises approximately 0.1% to approximately 5% by weight of a surfactant.

5. The method of claim 4, further comprising approximately 0.5% to approximately 5% by volume of a low molecular weight alcohol.

* * * * *